(12) United States Patent
Podgorski et al.

(10) Patent No.: US 8,066,751 B2
(45) Date of Patent: Nov. 29, 2011

(54) IMPLANTABLE ORTHOPAEDIC DEVICE, IN PARTICULAR FOR THE CERVICAL SPINE

(76) Inventors: Jean-Pierre Podgorski, Saint-Crespin-sur-Moine (FR); Guillaume Derouet, Saint-Herblain (FR)

(*) Notice: Subject to any disclaimer, the term of this patent is extended or adjusted under 35 U.S.C. 154(b) by 433 days.

(21) Appl. No.: 12/441,260

(22) PCT Filed: Sep. 11, 2007

(86) PCT No.: PCT/FR2007/051907
§ 371 (c)(1), (2), (4) Date: Mar. 13, 2009

(87) PCT Pub. No.: WO2008/031983
PCT Pub. Date: Mar. 20, 2008

(65) Prior Publication Data
US 2009/0318978 A1    Dec. 24, 2009

(30) Foreign Application Priority Data
Sep. 14, 2006 (FR) ..................... 06 08030

(51) Int. Cl.
*A61B 17/80* (2006.01)
(52) U.S. Cl. .................. 606/290; 606/289; 606/294
(58) Field of Classification Search .......... 606/289–291, 606/294
See application file for complete search history.

(56) References Cited

U.S. PATENT DOCUMENTS

| | | | | |
|---|---|---|---|---|
| 7,857,839 B2* | 12/2010 | Duong et al. | ................. | 606/290 |
| 7,909,860 B2* | 3/2011 | Rathbun et al. | ................. | 606/290 |
| 2004/0260306 A1 | 12/2004 | Fallin et al. | | |

OTHER PUBLICATIONS

International Search Report of PCT/FR2007/051907, date of mailing Mar. 25, 2008.

* cited by examiner

*Primary Examiner* — Thomas C. Barrett
*Assistant Examiner* — Andrew Yang
(74) *Attorney, Agent, or Firm* — Westerman, Hattori, Daniels & Adrian, LLP

(57) ABSTRACT

The invention relates to an implantable orthopaedic device, in particular for the cervical spine, of the type formed by a support plate (2) provided with at least one orifice (3) for passage of a fixing screw (4), which orifice (3) is provided with locking means comprising a slotted metal ring (8) accommodated in a receiving groove (5) on the circumference of said orifice (3) of the plate and intended to cooperate with an annular channel (10) formed in the screw head (4*a*). According to the invention, the annular chamber (10) of the screw head (4*a*) is framed by an end of male spherical contour (11') and by a truncated annular protuberance (12). This end of male spherical contour (11') is designed to cooperate with the complementary female spherical contour (7*a*') formed on the upper flange (7*a*) of the plate groove (5). Moreover, the locking ring (8) is mounted "floating" in its receiving groove (5), and the channel (10) of the screw head (4*a*) is connected to said annular protuberance (12) via a truncated part (10*c*) allowing the screw to be undone.

9 Claims, 5 Drawing Sheets

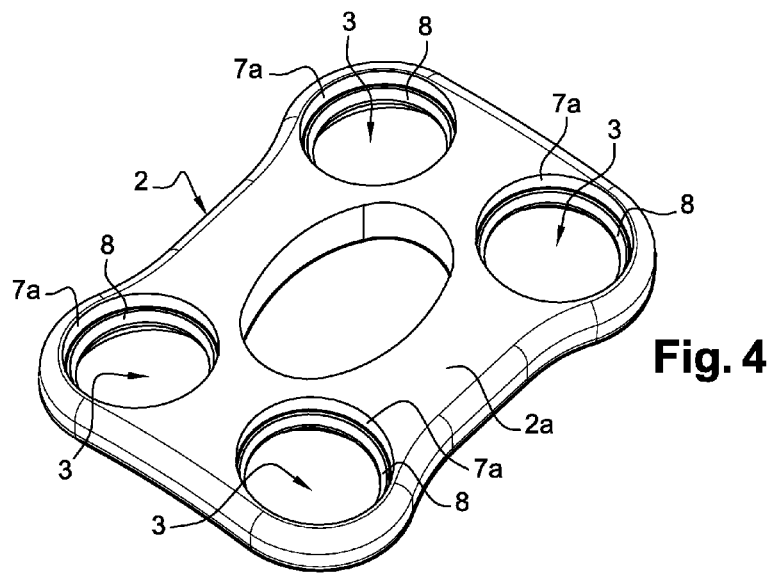
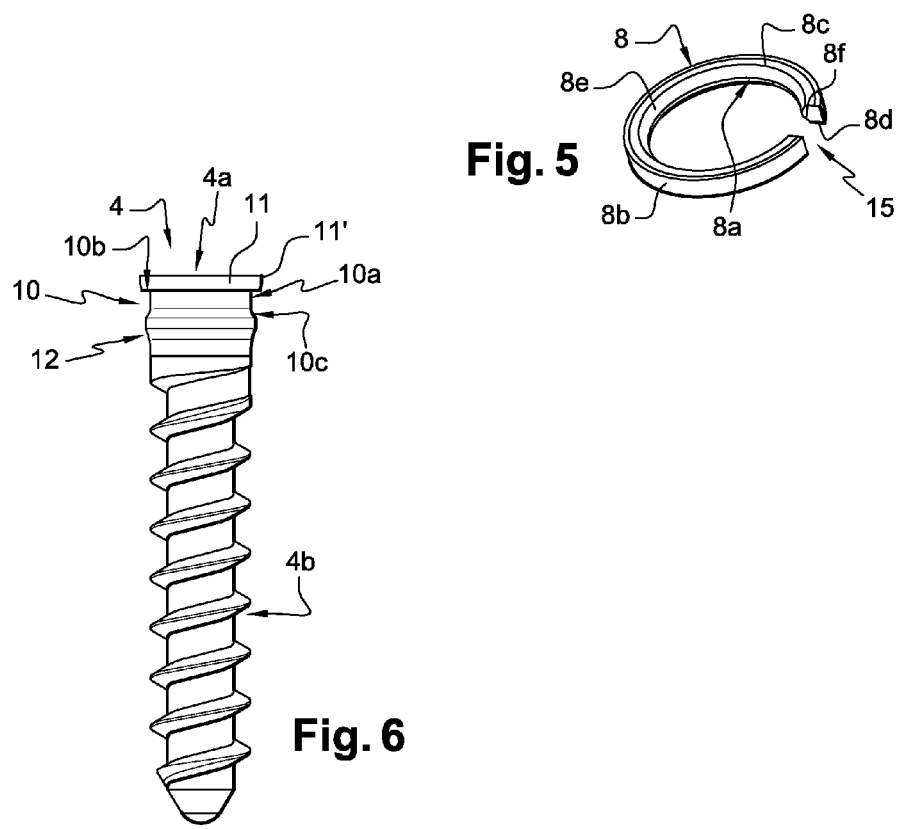

IMPLANTABLE ORTHOPAEDIC DEVICE, IN PARTICULAR FOR THE CERVICAL SPINE

BACKGROUND OF THE INVENTION

The present invention relates to a novel orthopaedic device, of the type formed by a support plate provided with at least one orifice for passage of a screw for fixing it to the receiving bone material, adapted in particular for being implanted in the cervical spine of a patient.

In case of intervertebral fusion (arthrodesis), a plate-shaped implant is generally used to consolidate the cervical spine and to ensure the position keeping of the bone graft placed by the practitioner between two vertebrae, in replacement of the intervertebral disk that has been extracted.

The corresponding plate is provided several orifices each intended to receive a fixing screw capable of anchoring in the receiving bone material. The shape and dimensions of this plate, and of the associated screws, are adapted to the treated site and to the implantation constraints.

Very generally, the support plates are proposed to the practitioner with a batch of screws of different sizes, only some of which are used depending on the implantation site.

For optimum efficiency and security, at the time of implantation, the practitioner applies a particular tightening to each screw, so that the associated plate is suitably positioned and maintained against the vertebrae.

Most of the present orthopaedic devices comprise means for locking or clamping the screws, so as to prevent or at least limit these screws from moving back with respect to the associated plate, after the assembly is reloaded (the corresponding loosening of the screws being liable to create discomfort to the patient or to imply high risks of lesion).

Such orthopaedic devices are described, for example, in U.S. Pat. No. 7,001,389 and US-2004/0260306. In these documents, the fixing screws each comprise a head provided with an annular channel within which a radially elastic locking ring is pre-mounted. As for the plate, it is provided with orifices whose internal surface is provided with a groove delimited by an upper annual material strip having a beveled top face, and a lower face forming an annular flat surface.

In practice, each screw is implanted through one of the orifices of the plate and screwed until its head automatically locks within the associated orifice. To this end, when the screw head reaches the upper edge of the groove, its spring ring is radially compressed by the above-mentioned beveled top surface, then it automatically expanses within this groove to form the required stop for preventing back-moving or unscrewing, with the above-mentioned annular flat surface. However, with such devices, it is necessary to equip each screw with a locking ring, namely both the screws that are implanted and those that are not used, which entails a not insignificant cost.

Moreover, once the screws implanted, it is not possible to remove them without damaging the material.

Another type of material of this sort is described in FR-2 778 088. Here, the screw backstop means consist of a slide slidingly mounted on the support plate, capable to partially cover the screw heads once the latter are suitably tightened. However, this structure is rather complex. Moreover, this type of implant necessitates additional operating time to insert or remove the screws, as well as additional equipment.

Further, the backstop means are inevitably efficient only on a well-defined area of the screw periphery.

U.S. Pat. No. 6,602,255 presents still other implants of this sort. In a possible embodiment, the corresponding implant is formed by a support plate provided with insertion orifices for the fixing screws, within which orifices is provided a receiving groove for an open locking ring, the latter two having general shapes that are complementary with each other. Under the groove equipped with its locking ring, each orifice is provided with a portion having a female spherical peripheral surface.

The fixing screws comprise a head extended by a threaded body. These screw heads are equipped with an annular peripheral protuberance or excrescence, having a male spherical surface that is complementary with the female spherical surface of the associated orifice of the plate, said protuberance connecting with the upper part of said screw head by a circular flat surface perpendicular to the screw axis.

During the implant setting, the fixing screws are tightened until the spherical surface of their annular protuberance is in contact with the complementary spherical surface of the support plate. Before this contact, the annular protuberance is forced through the slotted ring, making the latter radially expands within its receiving groove. After the upper circular flat surface of this protuberance has passed the slotted ring, the latter automatically recovers its rest position to form the required locking member (through plane contact between the annular flat surface of the screw and the lower face of the slotted ring).

The spherical contact surfaces between the plate orifices and the screw heads offer the practitioner a possibility of angularly adjusting the screw.

However, given the structure of this implant, when the axis of the screw is not merged with that of its receiving orifice, the contact between the annular flat surface of the screw heads and the locking ring is not optimum, which minimizes the rest surface area that serves to prevent the screw from moving back.

Further, the removal of the screws after implantation is not very easy to make and necessitates particular additional equipment. This implies an additional cost as for the material, and also an additional operating time.

SUMMARY OF THE INVENTION

The applicant has developed an alternative implant structure, which has for advantage to be simple, reliable and efficient. Further, this structure is easily reversible; the same plates and the same screws can be reset following a first try, without necessitating the use of additional equipment.

To this end, the implant according to the invention consists, on the one hand, of a support structure of the plate type, which is delimited by a top face and by a bottom face, and which is provided with at least one through-orifice, and on the other hand, of at least one screw having a screw head and a screw body. Said through-orifice is shaped so as to enable passage of said screw, the contact between said screw head and said plate being made through complementary spherical surfaces. The orthopaedic device is also of the type comprising added locking means, able to prevent or at least to limit the screw from moving back once its head suitably in rest on the plate, said locking means consisting of an annular groove formed in a portion of the height of the internal surface of the plate orifice, delimited by an upper annular flange and by a lower annular flange, within which groove is added a slotted metal ring having a radial elastic deformation ability and of which, at rest, - on the one hand, the internal edge has a diameter smaller than that of said orifice, and - on the other hand, the external edge has a diameter smaller than that of the bottom of said annular groove. Moreover, the screw head is of the type comprising an annular protuberance diverging from said screw body to an annular channel; said protuberance being shaped so as to enable, when said screw head moves forward within the associated orifice, radial expansion of the locking spring ring within its receiving groove, and then, in the final phase of screwing, accommodation of said spring ring within said screw annular channel, by elastic radial shrinkage, so as to form said backstop locking means.

Within the scope of such a structure, the implant according to the invention is characterized in that:

a—the orifice of the support plate is delimited by successively, from the top face of said support plate to the bottom face of the latter:

a1—a female spherical contact surface formed on the internal edge of the groove upper flange, a2—the locking-ring receiving groove, delimited by an upper annular shoulder, a cylindrical or substantially cylindrical bottom surface and a lower annular shoulder, said upper and lower shoulders extending perpendicular to the axis of the plate orifice and the distance a between them defining the thickness of said groove, and a3—the internal edge of the groove lower flange, this internal edge being oversized relative to the portion of the screw that is intended to come opposite, b—the screw head comprises successively, from its free end to the screw body:

b1—a male spherical contact surface, complementary with the female spherical surface of the support plate, b2—the annular channel for receiving the spring ring, delimited by a shoulder, perpendicular to the axis of the screw, a cylindrical or substantially cylindrical bottom surface, and a generally diverging truncated portion, and b3—the annular protuberance ending at the screw body, which protuberance has a generally diverging truncated shape from said screw body to said channel, with its minimum diameter smaller than that of the internal edge of the locking ring and its maximum diameter comprised between that of said ring internal edge and the minimum diameter of the plate orifice, c—further, the locking spring ring has a thickness b smaller than the thickness a of its receiving groove, to be provided with at least one axial degree of freedom within said groove.

This combination of features allows to obtain an efficient locking of the screws after tightening.

The locking ring, mounted "floating" in its receiving groove, enables to efficiently prevent the screw from moving back, with a rest surface area for the screw which is optimized thanks to its ability to self-align with respect to the axis of said screw and also to its ability to deform when in contact with the upper surface of the receiving groove.

Moreover, the diverging truncated portion of the channel formed in the screw head enables the screw to be undone by the practitioner, if need be, without damaging the plate or the slotted ring and with the use of only the screw setting equipment (operated in the reverse direction).

According to another feature, the bottom diameter of the annular groove of the orifice(s) of the support plate is at least equal to the maximum diameter of the annular protuberance of the screw head, added with twice the width of the associated spring ring, said ring width corresponding to the distance that separates the internal and external edges thereof.

Preferably, the spring ring is delimited by two flat annular surfaces parallel to each other, the spacing of which defines the thickness b of said ring. Further, the diameter of the ring internal edge is, at rest, advantageously greater than that of the bottom of the screw head annular channel, to facilitate insertion of the screw on the ring and to optimize self-alignment of the ring axis with respect to the screw axis.

Still preferably, the thickness b of the spring ring is smaller than the height of the annular channel of the screw head.

According to a preferential embodiment, the internal edge of the spring ring has a generally V-shaped section converging inwards, defining two converging sloping surfaces, a top one and a bottom one, respectively.

This feature facilitates the setting of the screw, and the possible undoing thereof.

According to a particularly advantageous embodiment variant, the internal edge of the support plate upper flange comprises a cylindrical thread formed in the female spherical contact surface.

Within the scope of this variant, at least one of the fixing screws proposed to the practitioner in complement of the above-described screw structure comprises, from its free end to the screw body:

a cylindrical end portion, provided with an external thread complementary with the thread formed in the internal edge of the support plate upper flange, an annular channel for receiving the spring ring, and an annular protuberance.

The upper annular shoulder of said channel is adapted to rest on the opposite face of the spring ring, which itself rests against the support plate lower flange, to obtain an integral screw/plate locking.

This feature offers the practitioner an alternative solution for screwing the support plate, to be used according to the needs, depending on the implantation site.

Still according to this variant, the external edge of the spring ring advantageously comprises a thread complementary with that of said upper flange, which allows the positioning of said locking ring within its receiving groove, after screwing through said plate thread.

This feature facilitates the positioning of the ring within its receiving groove.

BRIEF DESCRIPTION OF THE DRAWINGS

The invention will be further illustrated, without being in any way limited, by the following description of several possible embodiments given only by way of example and shown in the attached drawings, in which:

FIG. 4 is a perspective view of the support plate according to a possible embodiment of an orthopaedic device such as that schematically illustrated in FIGS. 1 to 3;

FIG. 5 is a perspective view of a locking ring intended to be pre-mounted in the support plate of FIG. 4;

FIG. 6 is a side view of one of the anchoring screws used to fix the plate of FIG. 4;

DETAIL DESCRIPTION OF THE PREFERRED EMBODIMENTS

Figure 1:
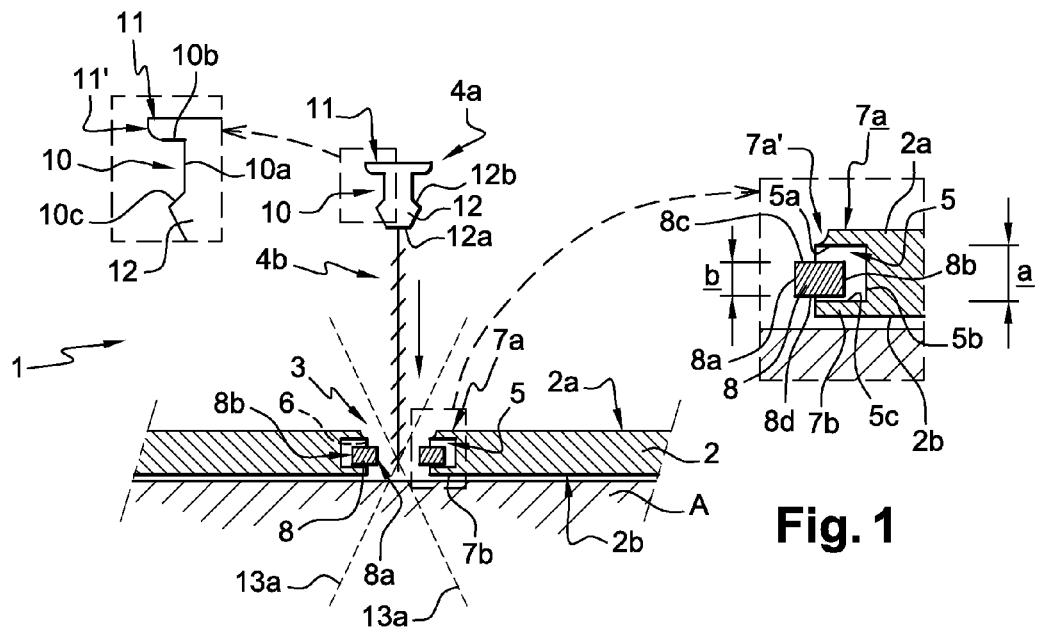
FIG. 1 is a schematic and functional view of an orthopaedic device according to the invention, in which the anchoring screw is suitably prepositioned for implantation through the orifice of a support plate which partially drawn.
Figure 2:
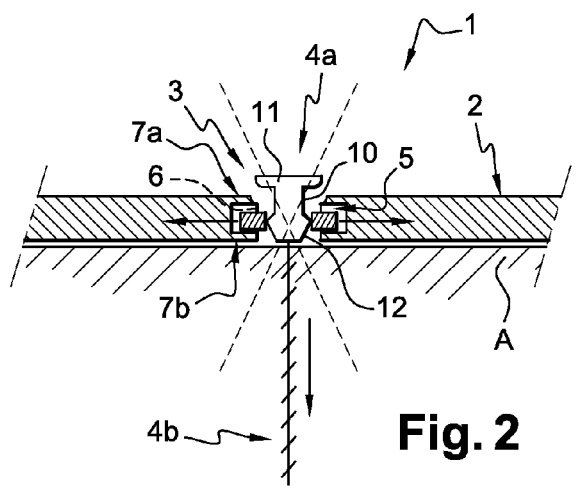
FIG. 2 is a schematic and functional view of the orthopaedic device according to FIG. 1, in which the screw arrives in the final phase of tightening.
Figure 3:
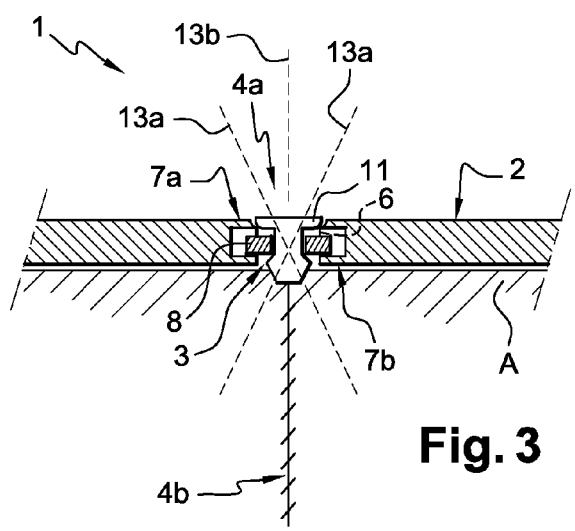
FIG. 3 is another schematic and functional view of the orthopaedic device according to FIGS. 1 and 2, in which the screw head is suitably locked within the support plate orifice.

As schematically show in FIGS. 1 to 3, the orthopaedic device 1 consists of a plate-shaped support structure (or receiving structure) 2, in which at least one circular orifice 3 is formed (extending between the top face 2a and bottom face 2b of the structure). Each of these orifices 3 is adapted to receive a screw 4 for fixing the plate 2 on the bone material A.

The orthopaedic device 1 is, for example, intended to be implanted between to vertebrae of the cervical spine, in case of arthrodesis. Its function is thus to consolidate the two vertebrae one relative to the other and to prevent expulsion of the intervertebral graft positioned by the practitioner.

The orthopaedic device 1 also comprises means for locking each screw 4 with respect to the plate 2, in particular to prevent them from loosening once they are suitably implanted into the receiving bone material, so as to prevent displacement of the screws and of the graft.

These locking means are pre-mounted within the orifices 3 of the plate 2, before setting of the screws 4.

In this case, the orifice 3 comprises an annular groove 5, formed in a portion of the height of its internal surface 6 (between the top face 2a and the bottom face 2b of the plate 2), delimited by a top flange 7a and a bottom flange 7b. It will be noticed that the internal edge 7a' of the top flange 7a has a generally female spherical shape, profiled so as to cooperate with a complementary portion formed on the screw head 4a, as will be more fully described later.

Thus, the groove 5 is delimited:
by a circular annular shoulder 5a, as an extension of the spherical internal edge 7a' of the top flange 7a,
by a cylindrical or substantially cylindrical bottom surface 5b, and
by a lower annular shoulder 5c.

The upper 5a and lower 5c shoulders are parallel to each other and extend perpendicular to the axis of the orifice 3; the distance a between them defining the thickness of the groove 5

A slotted ring 8 having a radial elastic deformation ability is pre-mounted within the annular groove 5 to form the locking means for the screw 4.

A rest, as shown in FIG. 1, it can be seen that the spring ring 8 comprises an internal edge 8a whose diameter is smaller than that of the orifice 3, and an external edge 8b whose diameter is comprised between that of the orifice 3 and that of the bottom 5b of the annular groove 5.

Thus, the spring ring 8 extends both partially within the annular groove 5 and within the volume of the orifice 3.

The spring ring 8 is further delimited by two flat annular surfaces parallel to each other, a top one 8c and a bottom one 8d, the spacing of which defines the thickness b of said ring 8. It can be noticed that this thickness b of the spring ring 8 is smaller than that a of the associated annular groove.

The screw 4 comprises a head 4a shaped so as to cooperate with screwing means operated by the practitioner, and a screw body 4b provided with a thread enabling it to be screwed into the receiving bone material.

The screw 4 is particular in that its head 4a comprises a peripheral annular channel 10 having, on either side:
on the side opposite to the screw body 4b, a free end portion 11 whose peripheral edge 11' has a generally male spherical shape, and
on the side of the screw body 4b, a protuberance 12 extending between said screw body 4b and the above-mentioned annular channel 10.

The upper spherical peripheral edge 11' of the screw head 4a forms a contact surface that is complementary with the internal edge 7a' of the upper flange 7a of the support plate 2.

The annular channel 10 is intended to receive the spring ring 8 of the plate 2, when the screw 4 reaches its final phase of screwing. This annular channel 10 has a generally trapezoid-shaped section, with a cylindrical or substantially cylindrical bottom surface 10a, extended by an upper annular shoulder 10b, on the side of the free end portion 11 of the screw head 4a, and by a truncated surface 10c diverging toward the screw body 4b.

The annular shoulder 10b extends perpendicular to the axis of the screw 4; the truncated surface 10c is inclined by an angle comprised between 30° and 60° with respect to the axis of said crew 4.

The cylindrical bottom surface 10a of the channel 10 has a diameter slightly smaller than the diameter (at rest) of the internal edge 8a of the spring ring 8, and a height greater than the thickness b of said ring 8.

The protuberance 12 is shaped so as to enable, during the final screwing phase of the screw 4, radial expansion of the spring ring 8 within its receiving groove 5 (FIG. 2), and then accommodation of said spring ring 8 within the annular channel 10, by elastic radial shrinkage (FIG. 3), so as to lock the screw 4 with respect to the plate 2.

It is well understood that, in case of slight unscrewing of the screw 4, the truncated surface 10c of the channel 10 will come in rest against the spring ring 8, the latter preventing the unscrewing to be continued.

The protuberance 12 of the screw head 4a has a generally truncated shape, diverging from the screw head 4b to the annular channel 10. This protuberance mainly comprises:
a first end 12a on the side of the screw body 4b, the diameter of which is smaller than that of the internal edge 8a of the ring 8 at rest, and
a second end 12b, on the side of the channel 10, the diameter of which is greater than that of this ring internal edge 8a.

In practice, the screw body 4b is inserted through the orifice 3 and the spring ring 8 associated thereto; the inclination of the screw 4 with respect to the plate 2 is chosen by the practitioner depending on the configuration of the implantation site, in the allowable orientation range delimited by the axes 13a. The median position, perpendicular to the support plate 2, is represented by the axis 13b, which is coaxial with the axis of the orifice 3 of the plate 2.

The shape and dimensions of the groove 5 and the ring 8 provide the latter with at least one axial degree of freedom within said groove 5, which is higher than a simple functional clearance, thus allowing self-centering of the screw 4 and of the ring 8, respectively, whatever the allowable orientation of the axis of the screw 4 relative to that of the orifice 3.

The screw 4 is then tightened by the practitioner in the receiving bone material A, until the spherical portion 11' of its head 4a rests on the complementary spherical surface 7a' of the top flange 7a of the orifice 3 (FIG. 3). These two complementary spherical contact surfaces 7a', 11' then ensure an optimal rest of the screw head 4a on the receiving plate 2, whatever the orientation of the screw with respect to the axis of the orifice 3, in the above-mentioned allowable angular sector. To allow such an angular adjustment of the screw 4, as can be seen in FIG. 3, the bulk of the protuberance 12 of the screw head 4a is slightly lower than that of the internal edge of the opposite bottom flange 7b. The thickness of the ring 8, smaller than that of the annular channel 10, also contributes to this angular adjustment possibility and optimizes the above-mentioned ring/screw self-centering.

During the final phase of screwing (FIG. 2), the screw head 4 enters through the orifice 3.

The protuberance 12 of the screw head 4a then interacts with the internal edge 8a of the spring ring 8, the later then undergoing a radial expansion (FIG. 2). To this end, the bottom diameter of the groove 5 is at least equal to the maximum diameter 12b of the protuberance 12, added with twice the width of the ring 8, this width corresponding to the distance between the internal 8a and external 8b edges.

The spring ring 8 progressively moves over the length of the protuberance 12 with the progression of the head 4a, up to the annular channel 10, within which it automatically radially shrinks, recovering its "rest" state (FIG. 3).

In the latter configuration, the ring 8 forms a means insuring a structural locking between the screw head 4a and the orifice 3 of the plate 2. Indeed, this ring forms a stop between the top flange 7a of the orifice 3 and the lower end 10c of the annular channel 10, via the ring 8; this locking allows to prevent, or at least to greatly limit, the screw 4 from moving back or unscrewing when the implant is reloaded.

A particular embodiment of the orthopaedic device 1 according to the schematic FIGS. 1 to 3 is shown in FIGS. 4 to 9.

In FIG. 4, it can be seen a support plate 2 in which are formed four orifices 3 each provided with a radially deformable ring 8, and through each of which an anchoring screw 4 is intended to pass for being implanted into the receiving bone material.

The support plate 2 is made, for example, of a material of the titanium TA6V type, with a thickness of the order of 2 mm. Its orifices 3 have, for example, a diameter of the order of 5 mm; each of them has an annular groove 5 having a height of the order of 1.1 mm and a peripheral diameter of 0.7 mm.

The locking rings 8 accommodated in the grooves 5 are made of a metallic material of the titanium TA6V type, and each comprise an opening 15 (FIG. 5) providing them with their radial elastic deformation ability.

Each of them has internal 8a and external 8b edges, whose diameters are 4.7 mm and 6 mm, respectively. Their thickness is 0.7 mm.

As can be seen in FIG. 5, these spring rings 8 have an internal edge 8a with a generally triangularly-shaped section, having an inwardly orientated centered tip. This particular shape defines two converging sloping surfaces, a top one 8e and a bottom one 8f, which favors the deformation ability of the ring and also optimizes the allowable orientation range of the axis of the screw 4 with respect to the axis of the orifice 3. The two corresponding sloping surfaces favor, for the one 8e, the setting of the screw 4, through cooperation with the protuberance 12, and for the other 8f, the undoing of the screw 4, through cooperation with the truncated surface 10c of the channel 10. Moreover, this V-shaped tip restricts the contact surfaces with the screw head 4a, which helps to limit frictions and optimizes transfer of the deformation forces.

Besides, in FIG. 6, it can be seen the screw 4 comprising:

on the one hand, a screw head 4a provided with the end portion 11 with its spherical contour 11' and with the protuberance 12, separated from each other by the annular channel 10, and on the other hand, a threaded screw body 4b.

As described hereinabove, the annular channel 10 has a generally trapezoid-shaped section, with a cylindrical bottom surface 10a, extended by the upper annular shoulder 10b (on the side of the free end 11) and by the truncated lower surface 10c (on the side of the protuberance 12).

As above-mentioned, the truncated surface 10c is here to form a sort of ramp for the radial expansion of the spring ring 8 accommodated in the channel 10, in particular to allow the undoing of the screw 4 by a simple operation of deliberate unscrewing.

By way of indication, the annular channel 10 comprises a bottom surface 10a having a diameter of the order of 4.5 mm and a height of 1 mm; the inclination of the diverging surface 10c is of the order of 45° with respect to the screw axis.

Besides, the protuberance 12 has a generally truncated shape whose minimum diameter is 4.5 mm and maximum diameter is of the order of 5 mm, with a height of the order of 1.5 mm.

Figure 7:
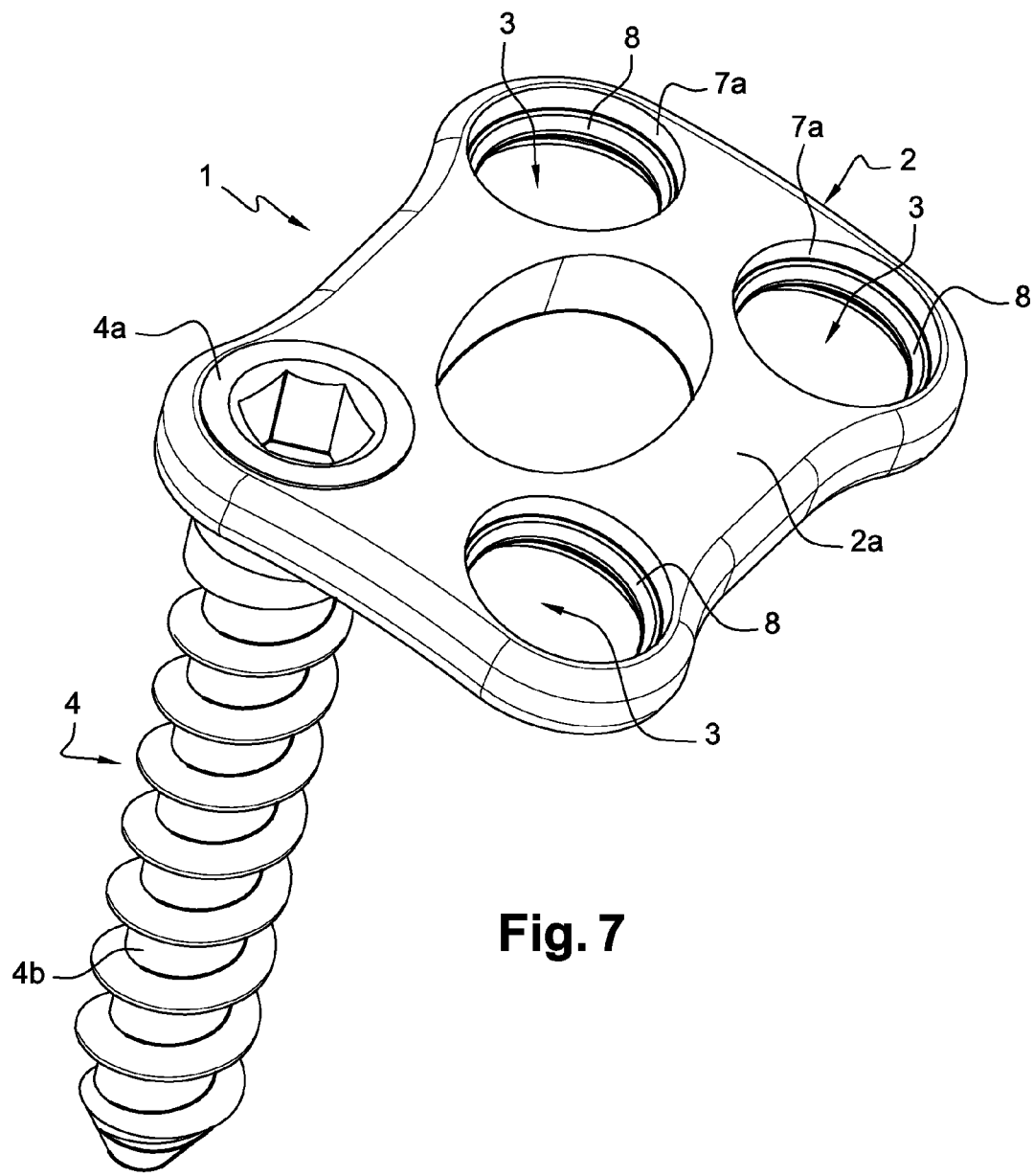
FIG. 7 is an overall perspective view of the screw of FIG. 6, suitably set through one of the receiving orifices of the support plate of FIG. 4.
Figure 8:
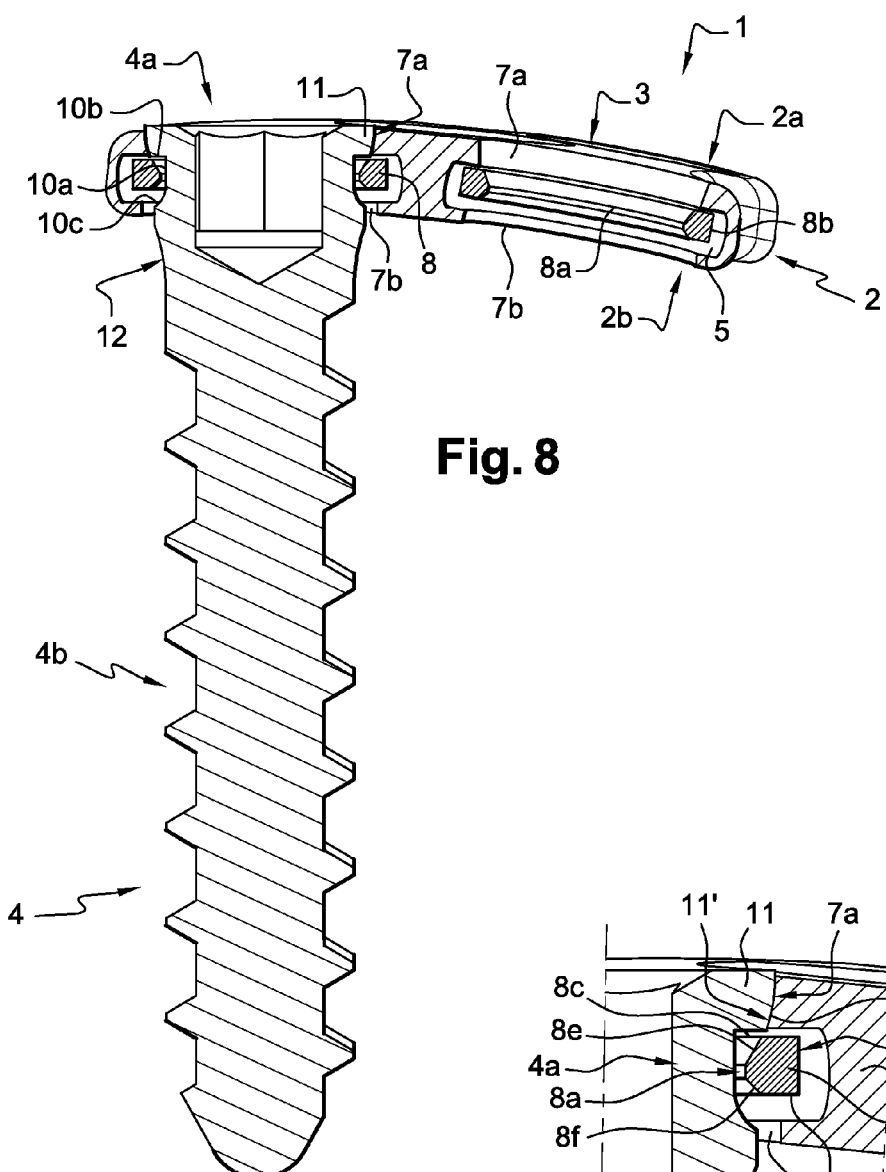
FIG. 8 is a cross-sectional view of the orthopaedic device of FIG. 7, taken along a plane passing through the axis of the screw, to show the locking of this screw on the support plate by a backstop means.
Figure 9:
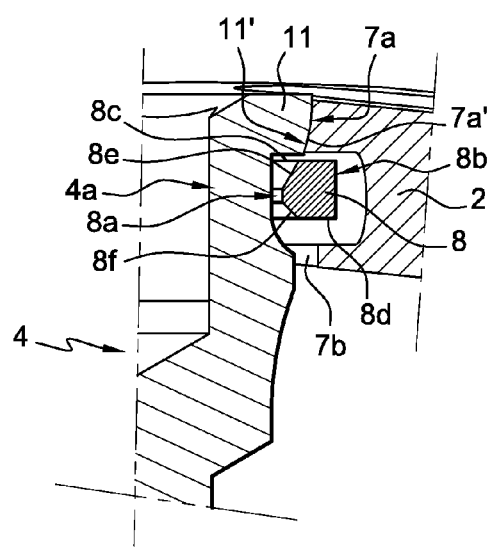
FIG. 9 is an enlarged view of a portion of FIG. 8 showing the locking ring positioned in the groove of the support plate and in the channel of the screw head.

As explained earlier, the implantation of the orthopaedic device 1 described above in relation with FIGS. 4 to 6 consists in inserting the screw body 4a of a screw 4 through one of the orifices 3 of the plate 2, and in screwing it into the bone material until the head 4a is placed within the above-mentioned orifice 3, in which it is automatically locked by the spring ring 8 (FIGS. 7, 8 and 9).

By way of indication, in this embodiment, the allowable amplitude for the axis of the screw 4 with respect to the axis of the orifice 3 is comprised between 10 and 20°.

The orthopaedic device according to the invention allows a simple and efficient locking of the screw 4 when the latter is suitably positioned by the practitioner in the receiving bone material. This screw can be undone. Further, the fact of positioning the locking rings on the support plate before setting the fixing screws allows simplification of the structure of the set of implantation pieces proposed to the practitioner.

Figure 10:
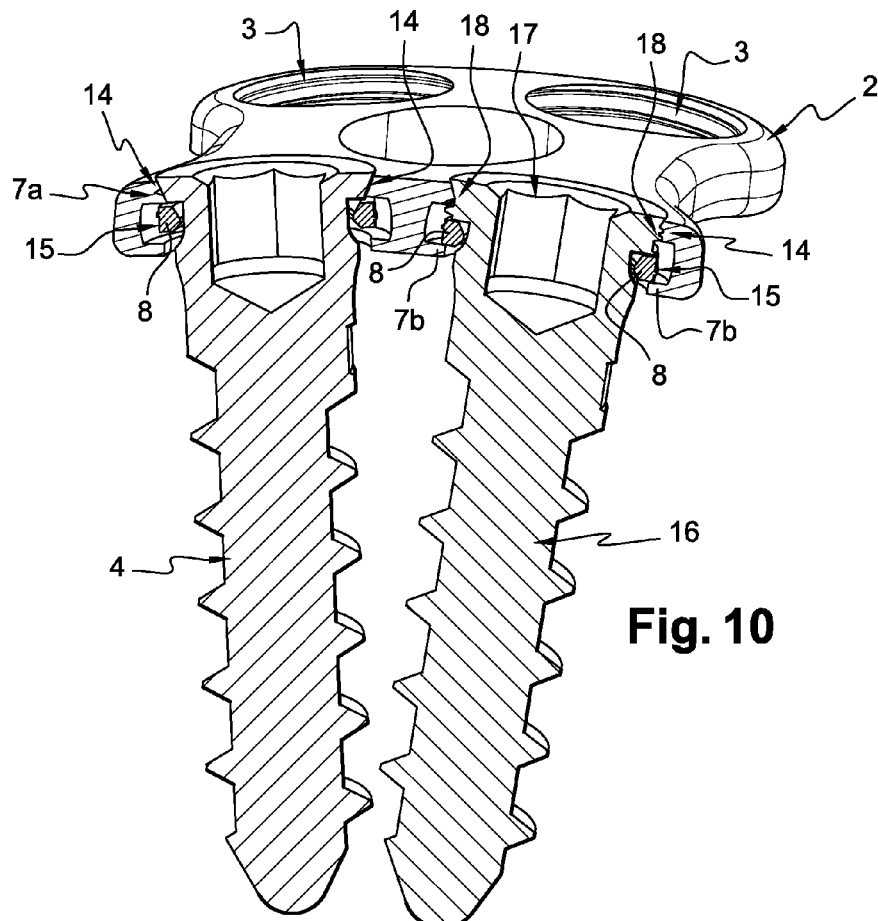
FIG. 10 is a cross-sectional and perspective view of a variant of the orthopaedic device according to the invention.
Figure 11:
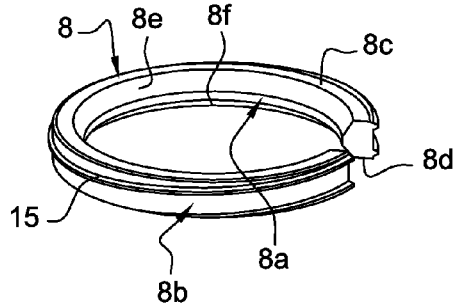
FIG. 11 is an isolated perspective view of the locking ring used within the scope of the implant embodiment of FIG. 10.
Figure 12:
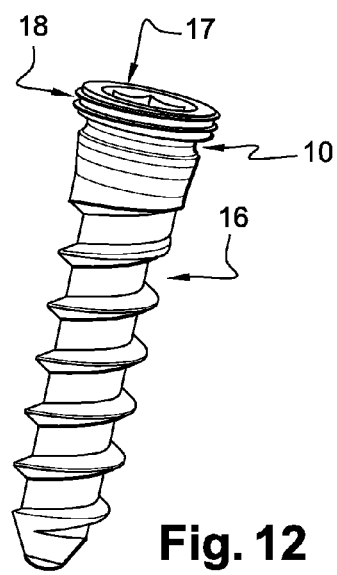
FIG. 12 is a perspective view of a particular screw, liable to be proposed to the practitioner in association with the fixing screws described in relation with the embodiment of FIGS. 1 to 9, within the scope of the variant illustrated in FIG. 10.

FIGS. 10 to 12 illustrate an embodiment variant of the implant.

As can be seen in FIG. 10, this variant differs from that illustrated in FIGS. 4 to 9 by the presence of a cylindrical thread 14 formed in the spherical contact surface 7a' of the plate 2, coaxially with the orifice 3.

The external edge 8b of the locking ring 8 then advantageously comprises a thread 15 complementary with said thread 14 of the plate.

Thus, the ring 8 is mounted on the support plate 2 by being screwed into the upper flange 7a of the plate, until it reaches the receiving groove 5 within which it falls and positions "floatingly".

It proves technically easier to position the ring 8 by screwing it, by comparison with inserting it by simple embedding (in particular because of the small dimensions of the involved pieces).

FIG. 11 shows an enlarged view of the corresponding locking ring 8, equipped with the thread 15 in its external edge 8b.

The thread 14 is hollowed out in the upper rim 7a of the support plate 2 and thus does in no way hinder the positioning of a fixing screw 4 such as above-described, as can be seen on the left in FIG. 10.

Moreover, the presence of the thread 14 advantageously allows to offer the practitioner one or more complementary screws 16 (in the batch of screws proposed with a set of plates), having a structure different from that of the above-described fixing screws 4, usable in particular to make an integral screw/plate assembly.

A possible embodiment of such a screw 16 is illustrated, as applied, on the right in FIG. 10, and isolated in FIG. 12.

This screw 16 is very similar to the above-described screws 4, the only difference being the replacement of the spherical end portion 11-11' by a cylindrical end portion 17 equipped with a peripheral external thread 18 complementary with the thread 14 of the plate.

As illustrated on the right in FIG. 10, this screw 16 can be screwed into the orifice 3 of the support plate 2 equipped with a locking ring 8. At the end of the screwing phase, the cylindrical end portion 17 of the screw 16 is screwed into the thread 14 of the upper flange 7a, until the upper annular shoulder 10b of the channel 10 rests on the locking ring 8, resting itself on the lower flange 7b.

Preferably, the pitch of the thread 18 is similar to that of the screw body thread; but it can be different, depending on the required mechanical effects.

An integral screw/plate assembly provided with a backstop means 8 is thus obtained.

It is well understood that this embodiment variant allows the application of two techniques for fixing the support plate, through the use of the fixing screws 4 and/or 16, which enables, depending on the surgical expectations, to obtain a constrained or semi-constrained system.

It will be noticed that, within the scope of this embodiment variant with the thread 14 in the plate, the locking ring 8 can exactly correspond to that described in relation with FIGS. 4 to 9, i.e. be deprived of the external thread 15.

The invention claimed is:

1. An orthopaedic device, in particular implantable in the cervical spine of a patient, said orthopaedic device comprising, on the one hand, a support structure of a plate type, which is delimited by a top face and by a bottom face, and which is provided with at least one through-orifice having a height and an internal surface, and on the other hand, of at least one screw having a screw head and a screw body, said through-orifice being shaped so as to enable passage of said screw, the contact between said screw head and said plate being made through complementary spherical surfaces, said orthopaedic device also comprising added locking means, able to prevent or at least to limit said screw from moving back once its head is suitably in rest on said plate, said locking means comprising an annular groove, formed in a portion of the height of the internal surface of said orifice, delimited by an upper annular flange, a lower annular flange and a bottom, in which groove is added a slotted metal ring, with an internal edge and an external edge, having a radial elastic deformation ability and of which, at rest, on the one hand, the internal edge has a diameter smaller than that of said orifice, on the other hand, the external edge has a diameter smaller than that of the bottom of said annular groove, said screw head comprising an annular protuberance diverging from said screw body to an annular channel , said protuberance being shaped so as to enable, when said head moves forward within said associated orifice, radial expansion of said ring within its receiving groove, and then, in the final phase of screwing, accommodation of said ring within said annular channel, by elastic radial shrinkage, so as to form said backstop locking means, wherein:
   a—the orifice of the support plate is delimited by successively, from the top face of said plate to the bottom face of the latter:
      a1 —a female spherical contact surface formed on an internal edge of said upper flange,
      a2 —said groove delimited by an upper annular shoulder, a cylindrical or substantially cylindrical bottom surface and a lower annular shoulder, said upper and lower shoulders extending perpendicular to an axis defined by the orifice and the distance between them defining the thickness of said groove, and
      a3 —an internal edge defined by said lower flange, the internal edge being oversized relative to a portion of said screw that is intended to come opposite,
   b—said screw head comprises successively, from a free end thereof to said screw body
      b1 —a male spherical contact surface, complementary with the female spherical surface of the upper flange of the annular groove of the orifice,
      b2 —said annular channel delimited by a shoulder perpendicular to a longitudinal axis defined by the screw, a cylindrical or substantially cylindrical bottom surface, and a generally diverging truncated portion, and
      b3 —said annular protuberance ending at said screw body, said protuberance having a generally diverging truncated shape from said screw body to said channel, with a minimum diameter smaller than that of the internal edge of said ring and a maximum diameter comprised between that of said internal edge of said ring and a minimum diameter of said orifice,
   c—the spring ring has a thickness smaller than the thickness of said groove in which it is accommodated, to be provided with at least one axial degree of freedom within said groove.

2. The orthopaedic device according to claim 1, wherein a diameter of the bottom of the annular groove of the orifice is at least equal to the maximum diameter of the protuberance, added with twice of a width defined by the associated ring, said width of the ring corresponding to a distance that separates the internal and external edges thereof.

3. The orthopaedic device according to claim 1, where the ring is delimited by two flat annular surfaces that are parallel to each other and a spacing therebetween defines the thickness of said ring.

4. The orthopaedic device according to claim 1, wherein the ring has an internal edge whose diameter at rest, is greater than that of a bottom defined by the annular channel of the screw head.

5. The orthopaedic device according to claim 1, wherein the ring has a thickness smaller than a height defined by the annular channel of the screw head.

6. The orthopaedic device according to claim 1, wherein the ring comprises an internal edge with a generally V-shaped section converging inwards, defining two converging sloping surfaces, a top one and a bottom one, respectively.

7. The orthopaedic device according to claim 1, wherein the internal edge of the upper flange of the support plate comprises a cylindrical thread formed in the female spherical contact surface.

8. The orthopaedic device according to claim 7, wherein it comprises at least one fixing screw, having a screw head and a screw body, the head of which comprises, from a free end to the screw body:
   a cylindrical end portion, provided with an external thread complementary with the thread formed on the internal edge of the upper flange of the annular groove of the orifice,
   an annular channel for receiving the ring, and
   an annular protuberance,
   an upper annular shoulder of said channel being adapted to rest on an opposing face of the ring, a face of which rests against the lower flange of the annular groove of said orifice, to obtain an integral screw/plate locking.

9. The orthopaedic device according to claim 1, wherein the external edge of the ring comprises a thread complementary with a thread of the upper flange of the orifice, so as to allow the positioning of the ring within its receiving groove, after screwing though the thread of the upper flange of the annular groove of the orifice.

* * * * *